(12) United States Patent
Bukowski et al.

(10) Patent No.: US 11,406,596 B2
(45) Date of Patent: *Aug. 9, 2022

(54) PROCESS FOR THE PREPARATION OF STERILE OPHTHALMIC AQUEOUS FLUTICASONE PROPIONATE FORM A NANOCRYSTALS SUSPENSIONS

(71) Applicant: Nicox Ophthalmics, Inc., Durham, NC (US)

(72) Inventors: Jean-Michel Bukowski, Villeneuve Leubet (FR); Akshay Nadkarni, Cary, NC (US); José L. Boyer, Chapel Hill, NC (US); Brigitte Duquesroix-Chakroun, Cagnes sur Mer (FR); Tomas Navratil, Durham, NC (US)

(73) Assignee: NICOX OPHTHALMICS, INC., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/934,807

(22) Filed: Jul. 21, 2020

(65) Prior Publication Data

US 2021/0023001 A1    Jan. 28, 2021

Related U.S. Application Data

(60) Provisional application No. 62/942,551, filed on Dec. 2, 2019, provisional application No. 62/877,599, filed on Jul. 23, 2019.

(51) Int. Cl.

| | |
|---|---|
| *A61K 9/08* | (2006.01) |
| *A61P 27/02* | (2006.01) |
| *A61K 9/00* | (2006.01) |
| *A61K 31/567* | (2006.01) |
| *A61K 47/02* | (2006.01) |
| *A61K 47/10* | (2017.01) |
| *A61K 47/18* | (2017.01) |
| *A61K 47/26* | (2006.01) |
| *A61K 47/38* | (2006.01) |
| *B82Y 5/00* | (2011.01) |

(52) U.S. Cl.
CPC ............. *A61K 9/08* (2013.01); *A61K 9/0048* (2013.01); *A61K 31/567* (2013.01); *A61K 47/02* (2013.01); *A61K 47/10* (2013.01); *A61K 47/183* (2013.01); *A61K 47/186* (2013.01); *A61K 47/26* (2013.01); *A61K 47/38* (2013.01); *A61P 27/02* (2018.01); *B82Y 5/00* (2013.01)

(58) Field of Classification Search
None
See application file for complete search history.

(56) References Cited

U.S. PATENT DOCUMENTS

| | | | | |
|---|---|---|---|---|
| 10,174,071 | B2 * | 1/2019 | Cavanagh | ............... A61P 27/14 |
| 2003/0194441 | A1 * | 10/2003 | Suzuki | ................. A61K 9/0048 424/488 |
| 2004/0204372 | A1 * | 10/2004 | Cohen | .................... A61K 45/06 514/35 |
| 2006/0229219 | A1 | 10/2006 | Zhi-Jian et al. | |
| 2006/0263123 | A1 * | 11/2006 | Blair | .................. G03G 15/2057 399/333 |
| 2015/0297614 | A1 * | 10/2015 | Ignar | ....................... A61P 37/08 514/171 |
| 2018/0022775 | A1 * | 1/2018 | Cavanagh | ............... A61P 11/06 514/180 |

FOREIGN PATENT DOCUMENTS

| | | |
|---|---|---|
| EP | 2847207 B1 | 3/2019 |
| WO | 9321903 A1 | 11/1993 |

OTHER PUBLICATIONS

International Search Report and Written Opinion dated Nov. 9, 2020 issued in corresponding PCT Application No. PCT/IC2020/056832.

\* cited by examiner

*Primary Examiner* — Katherine Peebles

(74) *Attorney, Agent, or Firm* — ArentFox Schiff LLP

(57) ABSTRACT

A process of manufacturing sterile topical ophthalmic aqueous nanosuspensions of nanocrystals of fluticasone propionate Form A. The sterile topical ophthalmic nanosuspensions may be used in the treatment of eye inflammation conditions such as blepharitis, posterior blepharitis, Meibomian gland dysfunction and dry eye through topical administration of said nanosuspensions to eyelids, eyelashes and eyelid margin.

25 Claims, 3 Drawing Sheets

PROCESS FOR THE PREPARATION OF STERILE OPHTHALMIC AQUEOUS FLUTICASONE PROPIONATE FORM A NANOCRYSTALS SUSPENSIONS

FIELD OF THE INVENTION

The present invention relates to a process for the preparation of sterile topical ophthalmic nanosuspensions containing nanocrystals of fluticasone propionate Form A in an aqueous vehicle. This process is readily adaptable to preparation for large-scale production and leads to sterile homogeneous aqueous nanosuspensions having a stable particle size distribution.

The sterile topical ophthalmic aqueous nanosuspensions containing fluticasone propionate Form A nanocrystals are useful in the treatment of eye inflammation diseases or eye inflammatory conditions through topical administration of said nanosuspensions (or nanocrystals suspensions) to eyelids (e.g. upper and lower lids), eyelashes and eyelid margin.

BACKGROUND OF THE INVENTION

Nanocrystals of fluticasone propionate Form A are nanoplates having the [001] crystallographic axis substantially normal to the surfaces that define the thickness of the nanoplates. The fluticasone propionate Form A nanocrystals are prepared from a commercially available fluticasone propionate polymorph 1 by the anti-solvent sonocrystallization process disclosed in WO 2013/169647.

WO 2013/169647 discloses the preparation of nanocrystals of a morphic form of fluticasone propionate (Form A), their purification and also the preparation of the aqueous suspensions containing said nanocrystals.

Briefly, according to the continuous sonicating flow-through scale-up process disclosed by WO 2013/169647 (Example 11 and FIG. 38) the nanocrystals of fluticasone propionate are prepared using antisolvent crystallization under sonication followed by the thermal annealing of the nanosuspension; the generated nanocrystals are purified by continuous flow centrifugation, the vehicle of the nanosuspension is centrifuged out, the pellet is re-dispersed in the washing solution and the dispersion centrifuged again. This washing procedure is repeated several times to achieve the desired level of purification. The pellet is then dispersed into the final formulation composition to obtain the final product at required dose strength. However, WO 2013/169647 does not report any data related to the sterility tests of the nanosuspension.

The applicant has found that the continuous sonicating flow-through process disclosed by WO 2013/169647 allows to prepare high amounts of fluticasone propionate Form A nanocrystals but it is not suitable for a large-scale preparation of sterile ophthalmic aqueous nanosuspensions because the dispersion of the purified nanocrystals (pellet) into the final aqueous vehicle (see FIG. 38) does not allow to produce a final product having the sterility requirements that must be met by pharmaceutical formulations for ocular delivery. Moreover, during the preparation of large-scale volumes of the nanosuspension it was found that, during the mixing of the purified nanocrystals with the final aqueous vehicle, the nanocrystals tended to form agglomerates that were difficult to be de-agglomerated therefore making difficulty to obtain homogeneous nanosuspensions. Moreover, even when some effective deaggregation and homogenous nanosuspensions were obtained extemporaneously, these nanosuspensions exhibited some propensity to reaggregate and to be unstable.

As it is well known, nanoparticles have a high propensity to agglomerate due to their high surface energy that cause the formation of agglomerates during the preparation and storage of the nanosuspensions.

Aggregation of the nanoparticles is not only a critical aspect during the manufacturing of the suspensions; agglomeration can cause a variety of issues, for example, inconsistent dosing and patient non-compliance. In particular, for nanosuspensions intended for application onto the eyelids, eyelashes and eyelid margin, agglomeration, may impact the tolerability in patients and potential safety.

Several strategies to ensure proper physical stability of drug nanosuspensions are well known.

For example, stabilizers are usually used, however, the selection of an appropriate stabilizer for a certain drug can be challenging.

US 2018/0117064 discloses the preparation of aqueous suspensions containing nanoparticles of a glucocorticosteroid compound and a dispersion stabilizer. US 2018/0117064 discloses that the main function of the stabilizer is to wet the drug particles thoroughly to prevent Ostwald ripening and agglomeration of the nanosuspension and to form a physically stable formulation by providing asteric or an ionic barrier. Typical examples of stabilizers used in nanosuspensions are celluloses, poloxamer, polysorbates, lecithin, polyoleate and povidones.

WO 2010/141834 discloses topical ophthalmic formulations of fluticasone propionate for treating allergic conjunctivitis and/or allergic rhinoconjunctivitis. WO 2010/141834 discloses a variety of formulations including suspensions having a particle size no greater than 30 μm; an example of vehicle comprises phosphate buffer, propylene glycol, hypromellose, polysorbate 80, edetate disodium and benzalkonium chloride (page 14, lines, 7-15).

However, WO 2010/141834 does not report any method of preparation of the ophthalmic formulations and any experimental results related to the stability of the ophthalmic formulations.

WO 2013/025696 discloses the use of high pressure homogenization to prevent formation of drug aggregates in an ophthalmic formulation containing an ophthalmic drug suspended in an aqueous vehicle containing at least one wetting agent. In particular the high pressure homogenization step may be used to prevent the formation of drug aggregates in the ophthalmic formulation when the drug particles are already present in a micronized form having particle sizes suitable for topical application; indeed WO 2013/025696 discloses that the high pressure homogenization may be applied to a suspension containing the pre-micronized drug in the aqueous solution of wetting agent and the high pressure homogenization does not bring about particle size reduction but instead stabilizes the already micronized drug, and thus prevent the formation of drug aggregates.

However, the process of WO 2013/025696 implies the use of high cost instruments that increases the cost of the dosage form, in addition, the use of high pressure homogenization could cause degradation of the nanocrystals.

The sonication process is commonly used for deagglomerating and dispersing nanomaterials in aqueous based media, necessary to improve homogeneity and stability of the suspension. Despite its widespread use, sonication treatment tested during the setting up of the process for the preparation of the nanosuspensions of the present invention was not effective to deagglomerate fluticasone propionate nanocrystals.

SUMMARY OF THE INVENTION

Therefore, there is a need to provide a large-scale process for the preparation of ophthalmic nanosuspensions (nanocrystals suspension) containing fluticasone propionate Form A nanocrystals in an aqueous vehicle.

As a result of studies performed to solve the above-mentioned problem, it was surprisingly found that mixing the nanocrystals of fluticasone propionate Form A with an aqueous vehicle containing glycerin (glycerol) and boric acid under high-shear, high speed conditions stabilizes the nanocrystals. Without wishing to be bound by any theory, it is believed that glycerin and boric acid form a complex that behaves as stabilizer of the nanocrystals; the boric acid/glycerol complex prevents the formation of nanocrystals aggregates during the preparation of the nanosuspensions and also stabilizes the nanosuspension during storage. The results of the studies also showed that adding the nanocrystals of fluticasone propionate Form A into the final vehicle containing the pre-formed boric acid/glycerol complex leads to a residual aggregation which is not observed when the nanosuspension is prepared according to the process of the present invention wherein glycerol is added after the nanocrystals of Fluticasone propionate are suspended and de-agglomerated in a vehicle that contains boric acid but no glycerol. When the nanocrystals of Fluticasone propionate are directly suspended and de-agglomerated in a final vehicle that contains the pre-formed boric acid/glycerol complex the stabilizing effect is lost and the de-agglomeration of the nanocrystals is more difficult to achieve and to maintain during the storage.

Complexes of boric acid with polyhydroxyl compounds (borate-polyol complexes) are well known and it is generally known the use of borate-polyol complexes in ophthalmic composition to enhance antimicrobial activity.

WO 93/21903 discloses borate-polyol complexes, such as mannitol, glycerol and propylene glycol, as adjunctive disinfecting agent in contact lens disinfecting solutions.

WO 2010/148190 discloses borate-polyol complexes including two different polyols to improve preservation of multi-dose ophthalmic compositions.

The present invention relates to a process for the preparation of sterile topical ophthalmic aqueous suspensions containing fluticasone propionate Form A nanocrystals that is readily adaptable to large-scale preparation for commercial production and gives rise to stable nanosuspensions with a homogenous reproducible particle size distribution.

For this invention "fluticasone propionate Form A nanocrystals" refer to fluticasone propionate Form A nanocrystals that have mean particle size from 100 nm to 1000 nm, a X-ray powder diffraction pattern including peaks at about 7.8, 15.7, 20.8, 23.7, 24.5, and 32.5 degrees 2$\Theta$, further including peaks at about 9.9, 13.0, 14.6, 16.0, 16.9, 18.1, and 34.3 degrees 2$\Theta$, and wherein the said nanocrystals are nanoplates having the [001] crystallographic axis substantially normal to the surfaces that define the thickness of the nanoplates.

DESCRIPTION OF THE INVENTION

Figure 1:
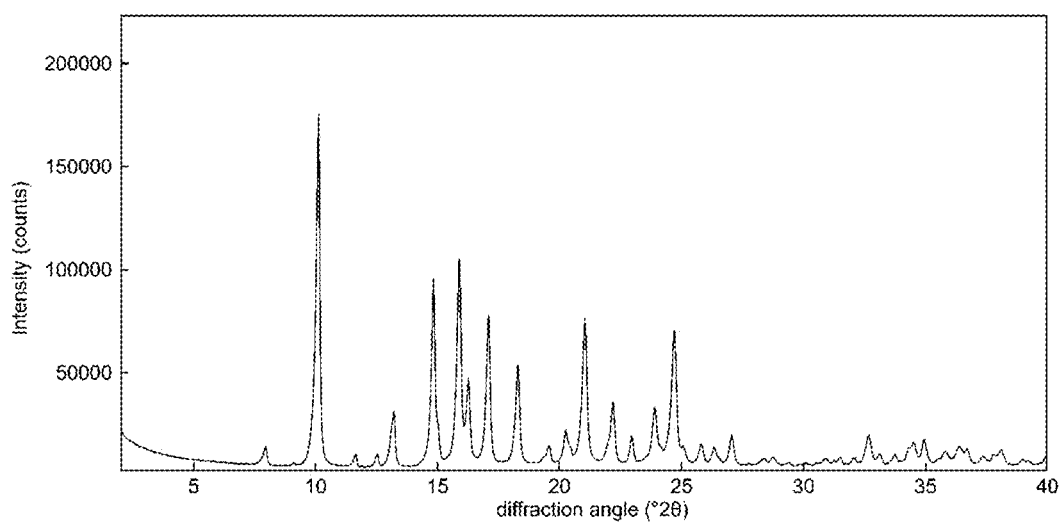
FIG. 1: the XRPD pattern of fluticasone propionate Form A nanocrystals

The present invention relates to a process for the preparation of sterile topical ophthalmic aqueous nanosuspensions containing fluticasone propionate Form A nanocrystals having a mean particle size from 100 nm to 1000 nm and a concentration of fluticasone propionate from 0.001% w/w to 1% w/w, said process comprises:

a) preparing an aqueous vehicle 1 containing: 0.5 w/w methylcellulose 4000 cp, 1.0% w/w boric acid, 0.1% w/w edetate disodium dihydrate, 0.055% w/w sodium chloride, 0.01% w/w benzalkonium chloride, 0.2% w/w polysorbate 80, hydrochloric acid 1N and/or sodium hydroxide 1N to adjust the pH at 7.3-7.5 and water to 100% w/w;

b) mixing an amount of fluticasone propionate nanocrystals form A having a mean particle size from 100 nm to 1000 nm with an amount of aqueous vehicle 1 to obtain a slurry containing a concentration of fluticasone propionate of 2% w/w;

c) applying high-shear high-speed mixing to the slurry of step b) for at least 10 minutes;

d) preparing an aqueous vehicle 2 containing: 1.8% w/w glycerin, 0.5% w/w methylcellulose 4000 cp, 1.0% w/w boric acid, 0.1% w/w edetate disodium dihydrate, 0.055% w/w sodium chloride, 0.01% w/w benzalkonium chloride, 0.2% w/w polysorbate 80, hydrochloric acid 1N and/or sodium hydroxide 1N to adjust the pH at 7.3-7.5 and water q.s. to 100% w/w;

e) adding an aliquot of the aqueous vehicle 2 to the slurry of step c) to obtain a concentration of fluticasone propionate of about 1% w/w;

f) applying high-shear, high-speed mixing to the slurry of step e) till to obtain the targeted mean particle size;

g) sterilizing the nanosuspension of step f) by autoclaving;

h) preparing an aqueous vehicle 3 containing: 0.9% w/w glycerin, 0.5% w/w methylcellulose 4000 cp, 1.0% w/w boric acid, 0.1% w/w edetate disodium dihydrate, 0.055% w/w sodium chloride, 0.01% w/w benzalkonium chloride, 0.2% w/w polysorbate 80, hydrochloric acid 1N and/or sodium hydroxide 1N to adjust the pH at 7.3-7.5 and water q.s. to 100% w/w; and sterilizing the aqueous vehicle 3 by filtration;

i) aseptically adding an aliquot of the sterile aqueous vehicle 3 to the sterilized nanosuspension of step g) to prepare a sterile topical ophthalmic aqueous nanosuspensions containing the targeted concentration of fluticasone propionate nanocrystals Form A;

wherein the nanocrystals of fluticasone propionate Form A have an X-ray powder diffraction pattern of said nanocrystals includes peaks at about 7.8, 15.7, 20.8, 23.7, 24.5, and 32.5 degrees 2⊖, further including peaks at about 9.9, 13.0, 14.6, 16.0, 16.9, 18.1, and 34.3 degrees 2⊖, and wherein the nanocrystals are nanoplates having the [001] crystallographic axis substantially normal to the surfaces that define the thickness of the nanoplates.

In step c) the high-shear, high speed mixing of the slurry containing the nanocrystals of fluticasone propionate form A and the aqueous vehicle 1, which does not contain glycerin, is conducted to ensure an even distribution of the fluticasone propionate nanocrystals to improve the homogeneity of the final nanosuspension.

Preferably in step c) and in step f) the high-shear, high-speed mixing is performed at 6000 RPM.

Preferably the high-shear, high-speed mixing of step f) is applied for at least 10 minutes.

Preferably the sterilization of step g) of the nanosuspension of step f) containing a concentration of fluticasone propionate of 1% w/w is performed by autoclaving the nanosuspension in glass bottles at about 122° C. for about 40 minutes.

Preferably the aqueous vehicles 1 and 2 are filtered through 0.2 μm filter before their use in step b) and step e) respectively.

Optionally the aqueous vehicle 2 containing glycerin 1.8% w/w may be prepared by adding to an aliquot of vehicle 1 filtered through 0.2 μm filter an amount of glycerin to obtain a final concentration of glycerin of 1.8% w/w.

Preferably in the final sterile topical ophthalmic aqueous nanosuspensions prepared according to the process of the invention the concentration of fluticasone propionate is from 0.001% to 0.5% w/w; more preferably the concentration of fluticasone propionate is 0.5% w/w, 0.25% w/w, 0.20% w/w, 0.10% w/w, 0.05% w/w, 0.03% w/w, 0.01% w/w or 0.005% w/w; most preferably the concentration of fluticasone propionate is 0.20% w/w or 0.10% w/w or 0.05% w/w.

Alternatively, the process of the present invention may be performed under fully aseptic manufacturing conditions utilizing sterilized Fluticasone propionate Form A nanocrystals and sterilized vehicles 1 to 3, accordingly another embodiment of the present invention relates to a process for the preparation of sterile topical ophthalmic aqueous nanosuspensions containing fluticasone propionate Form A nanocrystals having a mean particle size from 100 nm to 1000 nm and a concentration of fluticasone propionate from 0.001% w/w to 1% w/w, said process comprises:

a-1) sterilizing fluticasone propionate Form A nanocrystals having a mean particle size from 100 nm to 1000 nm;
  b-1) preparing an aqueous vehicle 1 containing: 0.5 w/w methylcellulose 4000 cp, 1.0% w/w boric acid, 0.1% w/w edetate disodium dihydrate, 0.055% w/w sodium chloride, 0.01% w/w benzalkonium chloride, 0.2% w/w polysorbate 80, hydrochloric acid 1N and/or sodium hydroxide 1N to adjust the pH at 7.3-7.5 and water q.s. to 100% w/w; and sterilizing said aqueous vehicle 1 by filtration;
  c-1) aseptically mixing an amount of sterilized fluticasone propionate nanocrystals form A with an amount of the sterilized aqueous vehicle 1 to obtain a slurry containing a concentration of fluticasone propionate of 2% w/w;
  d-1) applying high-shear, high-speed mixing to the slurry of step c-1) for at least 10 minutes;
  e-1) preparing an aqueous vehicle 2 containing: 1.8% w/w glycerin, 0.5% w/w methylcellulose 4000 cp, 1.0% w/w boric acid, 0.1% w/w edetate disodium dihydrate, 0.055% w/w sodium chloride, 0.01% w/w benzalkonium chloride, 0.2% w/w polysorbate 80, hydrochloric acid 1N and/or sodium hydroxide 1N to adjust the pH at 7.3-7.5 and water q.s. to 100% w/w; and sterilizing said aqueous vehicle 2 by filtration;
  f-1) aseptically adding an aliquot of the sterilized aqueous vehicle 2 to the slurry of step d-1) to obtain a concentration of fluticasone propionate of about 1% w/w;
  g-1) applying high-shear, high-speed mixing to the slurry of step f-1) till to obtain the targeted mean particle size;
  h-1) preparing an aqueous vehicle 3 containing: 0.9% w/w glycerin, 0.5 w/w methylcellulose 4000 cp, 1.0% w/w boric acid, 0.1% w/w edetate disodium dihydrate, 0.055% w/w sodium chloride, 0.01% w/w benzalkonium chloride, 0.2% w/w polysorbate 80, hydrochloric acid 1N/sodium hydroxide 1N to adjust the pH at 7.3-7.5 and water to 100% w/w; and sterilizing said aqueous vehicle 3 by filtration;
  i-1) aseptically adding an aliquot of the sterilized aqueous vehicle 3 to the nanosuspension of step g-1) to prepare a sterile topical ophthalmic aqueous nanosuspensions containing the final concentration of fluticasone propionate nanocrystals Form A;

wherein the nanocrystals of fluticasone propionate Form A have a X-ray powder diffraction pattern including peaks at about 7.8, 15.7, 20.8, 23.7, 24.5, and 32.5 degrees 2⊖, further including peaks at about 9.9, 13.0, 14.6, 16.0, 16.9, 18.1, and 34.3 degrees 2⊖, and wherein the nanocrystals are nanoplates having the [001] crystallographic axis substantially normal to the surfaces that define the thickness of the nanoplates.

Preferably the fluticasone propionate Form A nanocrystals used in step a-1) are sterilized by autoclaving a suspension of fluticasone propionate Form A nanocrystals in water for injection having a concentration of fluticasone propionate between 2% to 20% w/w; preferably the suspension of fluticasone propionate Form A nanocrystals in water is autoclaved at about 122° C. for about 30 minutes.

Preferably in step d-1) and step g-1) the high-shear, high-speed mixing is performed at 6000 RPM.

Preferably the high-shear, high-speed mixing of step g-1) is applied for at least 10 minutes.

Preferably in the sterile topical ophthalmic aqueous nanosuspensions prepared according to the process of the invention the concentration of fluticasone propionate is from 0.001% to 0.5% w/w; more preferably the concentration of fluticasone propionate is 0.5% w/w, 0.25% w/w, 0.20% w/w, 0.10% w/w, 0.05% w/w, 0.03% w/w, 0.01% w/w or 0.005% w/w; most preferably 0.20% w/w or 0.10% w/w or 0.05% w/w.

Preferably fluticasone propionate Form A nanocrystals used in the process of the present invention are prepared according to a general method reported below that comprises the following steps:

1) preparing a phase I solution comprising: 0.45% w/w fluticasone propionate polymorph 1, 23.2% w/w polyethylene glycol 400 (PEG 400), 68.8% w/w polypropylene glycol 400 (PPG 400), and 7.6% w/w polysorbate 80 (Tween 80); and filtering the phase I solution through 0.8/0.2 μm Polyethersulfone (PES) filter;

2) preparing a phase II solution comprising: 0.01% w/w benzalkonium chloride, 0.40% w/w methyl cellulose 15 cP, 0.1% w/w polyethylene glycol 40 stearate (PEG-40 stearate), citrate buffer to pH 3.4 to 3.8 and water q.s. to 100% w/w, and filtering the phase II solution through 0.8/0.2 μm Polyethersulfone (PES) filter;

3) cooling the filtered phase I and phase II solutions to a temperature from 0 to 4° C.;

4) mixing the phase I and the phase II solutions in a reactor equipped with ultrasonic transducer (for example QSonica Q2000 Ultrasonic transducer) to obtain a phase III suspension of nanocrystals, wherein:
  the phase I solution and the phase II solution are pumped continuously into the reactor at flow rates of 600 ml/min (phase I solution) and 2400 ml/min (phase II solution) respectively to obtain a phase III suspension;
  the volumes ratio phase I and phase II is 1:4;
  the sonication is applied during the mixing with an output power of 60%;
  the average temperature of phase III suspension is about 11° C.;

5) low shear mixing phase III suspension of step 4) at sufficient speed to create a vortex, at room temperature for a minimum of 30 minutes in absence of sonication;

6) annealing the phase III suspension at 40° C. over a period of time not less than 16 hours;

7) preparing a buffer solution comprising: 0.2% w/w polyethylene glycol 40 stearate (PEG-40 stearate), 0.2% w/w polysorbate 80 (Tween 80), 0.001% w/w benzalkonium chloride, 0.05% w/w sodium phosphate monobasic monohydrate, 0.02% w/w sodium phosphate dibasic dihydrate and water q.s. to 100% w/w, having a pH 6.3±0.2; and filtering the buffer solution through 0.8/0.2 μm Polyethersulfone (PES) filter;

8) diluting the phase III suspension of step 6) with the filtered buffer solution wherein the volumes ratio buffer solution and phase III is 1:1;

9) centrifuging the diluted phase III suspension to recover the fluticasone propionate nanocrystals Form A and washing the recovered nanocrystals;

10) washing the collected nanocrystals with water for injection.

When the process of the invention is performed under fully aseptic manufacturing conditions the washed nanocrystal of step 10) are sterilized before their use for the preparation of the sterile topical ophthalmic aqueous nanosuspensions; for example, the washed nanocrystals are suspended in water for injection at a fluticasone propionate concentration between 2% to 20% w/w, and autoclaved at about 122° C. for 30 minutes. Another embodiment of the present invention relates to an ophthalmic aqueous nanosuspension administrable topically onto eyelids, eyelashes or eyelid margin and consisting of:
  (a) 0.001% to 1% w/w fluticasone propionate Form A nanocrystals;
  (b) 0.50% w/w methylcellulose 4000 cp;
  (c) 0.2% w/w polysorbate 80;
  (d) 0.10% w/w edetate disodium dihydrate;
  (e) 1.0% w/w boric acid;
  (f) 0.9% w/w glycerin;
  (g) 0.01% w/w benzalkonium chloride;
  (h) 0.055% w/w sodium chloride;
  (i) hydrochloric acid (1N) and/or sodium hydroxide (1N) as adjusting agents in an amount sufficient pH from 7.3-7.5; and
  (j) water q.s. to 100% w/w,
wherein said nanocrystals of fluticasone propionate Form A have a mean particle size from 100 nm to 1000 nm and a X-ray powder diffraction pattern including peaks at about 7.8, 15.7, 20.8, 23.7, 24.5, and 32.5 degrees 2Θ, further including peaks at about 9.9, 13.0, 14.6, 16.0, 16.9, 18.1, and 34.3 degrees 2Θ, and wherein the nanocrystals are nanoplates having the [001] crystallographic axis substantially normal to the surfaces that define the thickness of the nanoplates.

Preferably, in the topical ophthalmic aqueous nanosuspension the concentration of fluticasone propionate is from 0.001% to 0.5% w/w, more preferably the concentration of fluticasone propionate is 0.5% w/w, 0.25% w/w, 0.20% w/w, 0.1% w/w, 0.05% w/w, 0.03% w/w, 0.01% w/w or 0.005% w/w. Most preferably in the topical ophthalmic aqueous nanosuspension the concentration of fluticasone propionate is 0.1% w/w, 0.20% w/w or 0.05% w/w.

Another embodiment of the present invention relates to an ophthalmic aqueous nanosuspension administrable topically onto eyelids, eyelashes or eyelid margin and consisting of:
  (a) 0.1% w/w, or 0.5% w/w, or 0.25% w/w, or 0.20% w/w or 0.05% w/w fluticasone propionate Form A nanocrystals;
  (b) 0.50% w/w methylcellulose 4000 cp;
  (c) 0.2% w/w polysorbate 80;
  (d) 0.10% w/w edetate disodium dihydrate;
  (e) 1.0% w/w boric acid;
  (f) 0.9% w/w glycerin;
  (g) 0.01% w/w benzalkonium chloride;
  (h) 0.055% w/w sodium chloride;
  (i) hydrochloric acid (1N) and/or sodium hydroxide (1N) as adjusting agents in an amount sufficient pH from 7.3-7.5; and
  (j) water q.s. to 100% w/w,
wherein said nanocrystals of fluticasone propionate Form A have a mean particle size from 100 nm to 1000 nm and a X-ray powder diffraction pattern including peaks at about 7.8, 15.7, 20.8, 23.7, 24.5, and 32.5 degrees 2Θ, further including peaks at about 9.9, 13.0, 14.6, 16.0, 16.9, 18.1, and 34.3 degrees 2Θ, and wherein the nanocrystals are nanoplates having the [001] crystallographic axis substantially normal to the surfaces that define the thickness of the nanoplates.

Another preferred embodiment of the present invention relates to an ophthalmic aqueous nanosuspension administrable topically onto eyelids, eyelashes or eyelid margin and consisting of:
  (a) 0.1% w/w, or 0.20% w/w or 0.05% w/w fluticasone propionate Form A nanocrystals;
  (b) 0.50% w/w methylcellulose 4000 cp;
  (c) 0.2% w/w polysorbate 80;
  (d) 0.10% w/w edetate disodium dihydrate;
  (e) 1.0% w/w boric acid;
  (f) 0.9% w/w glycerin;
  (g) 0.01% w/w benzalkonium chloride;
  (h) 0.055% w/w sodium chloride;
  (i) hydrochloric acid (1N) and/or sodium hydroxide (1N) as adjusting agents in an amount sufficient pH from 7.3-7.5; and
  (j) water q.s. to 100% w/w,
wherein said nanocrystals of fluticasone propionate Form A have a mean particle size from 100 nm to 1000 nm and a X-ray powder diffraction pattern including peaks at about 7.8, 15.7, 20.8, 23.7, 24.5, and 32.5 degrees 2Θ, further including peaks at about 9.9, 13.0, 14.6, 16.0, 16.9, 18.1, and 34.3 degrees 2Θ, and wherein the nanocrystals are nanoplates having the [001] crystallographic axis substantially normal to the surfaces that define the thickness of the nanoplates.

The sterile topical ophthalmic aqueous nanosuspensions prepared according to the process of the present invention have some advantages, for example better tolerability upon administration onto eyelids (e.g. the upper and lower eyelids), eyelashes or eyelid margin due to the small particles sizes and maintenance of drug release over a prolonged period of time that allows reducing the amount of the active principle to be administered and, consequently, reducing the systemic exposure to fluticasone propionate as well as reducing the exposure to other structure of the eye. As it is well known, corticosteroids have side effects such as the increase of the intra-ocular pressure (IOP), the increase of corneal thickness, mydriasis, ptosis, cataract, glaucoma, adrenal suppression, decrease in bone mineral density; therefore low systemic exposure an overall eye are an important advantages of the ophthalmic aqueous nanosuspensions prepared according to the process of the present invention in particular for therapeutic applications that require long-term or repetitive corticosteroid treatment.

The sterile topical ophthalmic aqueous nanosuspension of the present invention has high efficacy and local tolerability without the unwanted side-effects associated with the systemic absorption of the fluticasone propionate active ingredient.

In another embodiment, the nanosuspension of the present invention may be used in a method for treating or reducing the symptoms and/or clinical signs associated with eye inflammation diseases or eye inflammatory conditions such as blepharitis, posterior blepharitis, Meibomian gland dysfunction or dry eye disease by topical administration of said composition to the eye lids, eye lashes or eye lid margin of a subject in need. Such method for treating blepharitis, posterior blepharitis, Meibomian gland dysfunction or dry eye disease comprises the step of topically administering to a subject's eyelids, eyelashes or eyelid margin an effective amount of the nanosuspension of the present invention.

Another embodiment of the invention provides a method of treatment and or reducing the symptoms and/or clinical signs associated with blepharitis, posterior blepharitis, Meibomian gland dysfunction or dry eye disease, the method comprising administering an effective amount of a pharmaceutical composition to a subject in need thereof wherein the pharmaceutical composition is an ophthalmic aqueous nanosuspension consisting of: 0.001% to 1% w/w nanocrystals of fluticasone propionate Form A, 0.50% w/w methylcellulose 4000 cp, 0.2% w/w polysorbate 80, 0.10% w/w edetate disodium dihydrate, 1.0% w/w boric acid, 0.9% w/w glycerin, 0.01% w/w benzalkonium chloride, 0.055% w/w sodium chloride, hydrochloric acid 1N and/or sodium hydroxide 1N as adjusting agents in an amount sufficient pH from 7.3-7.5, and water q.s. to 100% w/w, wherein said nanocrystals of fluticasone propionate Form A have a mean particle size from 100 nm to 1000 nm and a X-ray powder diffraction pattern including peaks at about 7.8, 15.7, 20.8, 23.7, 24.5, and 32.5 degrees 2$\Theta$, further including peaks at about 9.9, 13.0, 14.6, 16.0, 16.9, 18.1, and 34.3 degrees 2$\Theta$, and wherein the nanocrystals are nanoplates having the [001] crystallographic axis substantially normal to the surfaces that define the thickness of the nanoplates, wherein the ophthalmic aqueous nanosuspension is administered topically to the upper and/or lower eye lid margins, Meibomian gland ducts eyelashes or any area of the eye lid anatomy. Preferably the ophthalmic aqueous nanosuspension used in the method of the invention contain a concentration of fluticasone propionate Form A nanocrystals of 0.5% w/w, 0.25% w/w, 0.20% w/w, 0.10% w/w, 0.05% w/w, 0.03% w/w, 0.01% w/w or 0.005% w/w; more preferably the concentration of fluticasone propionate Form A nanocrystals in the ophthalmic aqueous nanosuspension is of 0.1% w/w, 0.20% w/w 0.25% w/w, 0.5% w/w, 0.05% w/w or 0.01% w/w; most preferably the concentration of fluticasone propionate Form A nanocrystals is 0.1% w/w, 0.20% w/w or 0.05% w/w.

Typical clinical signs associated with blepharitis and Meibomian gland dysfunction include lid debris, redness of eyelid margin, eyelid swelling, obstruction of the Meibomian gland, and or qualitative/quantitative changes in Meibomian gland secretion.

The most common symptoms associated with dry eye, which is also known as keratoconjunctivitis sicca, include eye dryness, eye discomfort, eye redness, a stinging, burning or scratchy sensation in the eyes, watery eyes, sensitivity to light, blurred vision, pain or eye fatigue.

The method of the invention is preferably directed to a method for treating non-infectious, inflammatory blepharitis or Meibomian gland dysfunction in a subject.

In another embodiment, a subject is administered with topical ophthalmic aqueous nanosuspension of the present invention at least once a day, preferably subject is administered with the pharmaceutical formulation once a day.

In another embodiment, a subject is administered with topical ophthalmic aqueous nanosuspension of the present invention at least once a day for at least two weeks, more than two weeks, at least three weeks, or at least four weeks.

Another embodiment of the present invention relates to a kit comprising (a) the above reported topical administrable ophthalmic aqueous nanosuspension containing fluticasone propionate Form A nanocrystals and (b) a swab or sponge to apply the nanosuspension to the eyelids, eyelashes or eyelid margin.

EXAMPLES

The percentage (%) as used herein in the compositions and in the examples refers to weight percentage (w/w) unless otherwise stated. The terms glycerin and glycerol in the text and in the examples are used as synonyms.

Example 1

Preparation of Nanocrystals of Fluticasone Propionate Form A

Preparation of Phase I Solution

In a 2 L process vessel, 106.26 g polysorbate 80 (Tween 80), 963.34 g polypropylene glycol 400 (PPG 400), 324.10 g polyethylene glycol 400 (PEG 400), were added at room temperature and stirred together until all components were dissolved, then 6.3 g fluticasone propionate polymorph 1 was added into the solution and stirred until a clear solution was obtained. The obtained solution was filtered using a 0.8/0.2 μm Polyethersulfone (PES) filter and kept refrigerated at 2-8° C. until use.

Preparation of Phase II Solution

In an 8 L process vessel an initial quantity of about 5276 g of purified water was added and stirred with an over-head mixer so that a vortex was generated.

6.01 g polyethylene glycol 40 stearate (PEG-40 stearate), 5.98 g benzalkonium chloride (solution 10%), and 24.02 g methyl cellulose 15 cP were added and stirred till methyl cellulose was completely dissolved. Citrate buffer was added to adjust the pH to 3.5-4.0 and 585.8 g water were added. The final pH of the phase II solution was 3.83

Phase II was then filtered using a 0.8/0.2 μm Polyethersulfone (PES) filter and kept refrigerated at 2-8° C. until use.

Preparation of Dilution Buffer Solution

In a 20 L process vessel, 12.0 g polysorbate 80 (Tween 80) were introduced, 5374 g purified water were added, and stirred with an over-head mixer so that a vortex was generated.

3.24 g sodium phosphate monobasic monohydrate, 1.14 g sodium phosphate dibasic dihydrate, 12.00 g polyethylene glycol 40 stearate (PEG-40 stearate), 0.6 g benzalkonium chloride (solution 10%) were added and stirred until complete dissolution, and 597 g water were added. The final pH of the buffer solution was 6.4. This solution was filtered using a 0.8/0.2 μm Polyethersulfone (PES) filter and kept refrigerated at 2-8° C. until use.

Preparation of Nanocrystal of Fluticasone Propionate Form A 480 g of phase II were introduced into the chamber of the reactor. 940 g phase I and 3780 g phase II were allowed to cool down to a target temperature of 2-4° C. in their jacketed vessels connected to chillers.

Using peristaltic calibrated pumps phase I and phase II were pumped (pump flow rates for phase I and phase II were respectively 600 ml/min and 2400 ml/min) through the reactor fitted with its ultrasonic transducer with an amplitude set at 60% (Q Sonica Q1375 W).

The outflow from the reactor (phase III: 5201.7 g) was collected into a clean vessel at room temperature. The temperature of phase III was about 11° C.

Then phase III was stirred at room temperature for about 30 minutes in the collecting vessel to obtain a uniform suspension of fluticasone propionate nanocrystals (final phase III).

Annealing Process

The final phase III was transferred into a closed container. The container was placed in an incubator and maintained at 40° C. for at least 16 hours.

Purification and Iolation of Nanocrystals 5167 g of the annealed phase III were transferred into a process vessel and an equivalent amount of dilution buffer solution was added, so that the ratio of phase III to dilution buffer solution was 1:1. The resulting mixture was stirred with a low shear mixer for 30 minutes to achieve a homogeneous suspension of nanocrystals (diluted phase III).

The diluted phase III was kept refrigerated at 2-8° C. until centrifugation.

The fluticasone propionate Form A nanocrystals were first collected by discontinuous centrifugation of the diluted phase III. The nanocrystals were then washed several times (4 washing cycles) with water for injection.

The particle size of the isolated nanocrystals was evaluated using a laser scattering Particle size distribution analyzer (Horiba LA-950). The $D_{50}$ was 0.2153 μm and the $D_{90}$ was 0.6073 μm Characterization of the nanocrystals was performed by XRPD and Rietveld refinement. Results are provided in FIG. 1 (XRPD) showing the typical pattern of Fluticasone propionate form A, having a crystal habit with strong preferred orientation and c-axis substantially normal to the surface, as defined in WO 2013/169647 confirmed by pole figure obtained from Rietveld refinement.

Example 2

Preparation of a Sterile Topical Ophthalmic Aqueous Nanosuspension of Fluticasone Propionate Form A

TABLE 1

| Fluticasone propionate nanosuspension composition | |
|---|---|
| Ingredients | Amount (% w/w) |
| Fluticasone propionate Form A nanocrystals | 0.10 |
| Methylcellulose 4000 cP | 0.50 |
| Polysorbate 80 | 0.2 |
| Edetate disodium, dihydrate | 0.10 |
| Boric acid | 1.0 |
| Glycerin | 0.9 |
| Benzalkonium chloride | 0.01 |
| Sodium chloride | 0.055 |
| Water for injection | q.s. to 100 % |
| pH | 7.3-7.5 |

Step 1) Preparation of Vehicle 1 (Vehicle without Glycerin)

In a 20 L process vessel, 17600 g water for injection were heated at 80° C., 100.0 g methylcellulose 4000 cp were slowly added and the mixture is stirred until methylcellulose was dissolved.

The solution was cooled at 40° C., 200.0 g boric acid was added and the pH was adjusted at 7.4 with sodium hydroxide (1N).

The following excipients were added in the specific following order: 20.0 g edetate disodium dihydrate, 11.0 g sodium chloride, 4.0 g benzalkonium chloride (solution 50%), 40.0 g polysorbate 80 (Tween 80); each excipient being fully dissolved before adding the next excipient and the preparation of the solution is carried out at a temperature of about 40° C. to room temperature. The pH was tested and optionally adjusted at 7.3-7.5 with hydrochloric acid (1N) or sodium hydroxide (1N); after the pH adjustment, water for injection was added to bring the final weight to 19800 g. The resulting solution was mixed for at least 10 minutes to obtain a uniform solution which was stored at 2-8° C.

Step 2) Preparation of the 2% Fluticasone Propionate Nanocrystals Slurry 4000 g of vehicle 1 were introduced into a 10 L process vessel containing a stir bar, by filtration through a PES 0.2 μm media and were set aside for further use.

In a 2 L beaker, 15.04 g of the fluticasone propionate Form A nanocrystals were introduced together with some vehicle 1. This slurry was mixed for homogeneity and assayed for fluticasone propionate content (31.6 mg/g), then it was further diluted with vehicle 1 so as to achieve a target concentration of fluticasone propionate of 20 mg/ml (2% w/w slurry). This concentrated slurry was subject to high-shear, high-speed mixing at 6000±10 RPM for 10 minutes and the particle size distribution was tested by laser diffraction on a Horiba LA-950S2 PSD analyzer.

The results were the following:
Mean: 0.856 μm
Mode: 0.363 μm
Median: 0.420 μm
$D_{10}$: 0.203 μm
$D_{90}$: 2.154 μm Step 3) Preparation of Vehicle 2 (Vehicle Containing Glycerin 1.8% w/w)

In a 4 L beaker, 1600 g of the filtered vehicle 1 were introduced, and 36 g glycerin were added under stirring until dissolution.

The pH was tested and adjusted at 7.3-7.5 with sodium hydroxide (1N) and vehicle 1 was further added to adjust the final weight to 2000 g, leading to a 1.8% w/w glycerin solution.

Step 4) Preparation of the 1% Fluticasone Propionate Nanocrystals Slurry

The 1% fluticasone propionate nanocrystals slurry was prepared by further diluting the 2% concentrated slurry prepared in Step 2) with vehicle 2 down to a concentration of fluticasone propionate of 1% w/w.

The 1% w/w fluticasone propionate Form A nanocrystals slurry was subject to high-shear, high-speed mixing at 6000±10 RPM for 10 minutes and the particle size distribution was tested by laser diffraction using a Horiba LA-95052 PSD analyzer.

The results were the following:
Mean: 0.428 μm
Mode: 0.123 μm
Median: 0.162 μm
$D_{10}$: 0.082 μm
$D_{90}$: 0.678 μm Aliquots of the 1% concentrated slurry were filled into 500 ml glass bottles containing stir bar and sterilized by autoclaving at 121.5° C. for 40 minutes.

Step 5) Preparation of Vehicle 3 (Vehicle Containing Glycerin 0.9% w/w)

In a 20 L container, 11200 g of vehicle 1 were introduced, 126 g of glycerin were added under stirring and the pH was then adjusted with sodium hydroxide to 7.3-7.5 and an aliquot of vehicle 1 was further added to adjust the final weight to 14000 g, leading to a 0.9% w/w glycerol solution. This solution was mixed for at least 10 minutes until uniform and sterile filtered into another receiving vessel.

Step 6) Preparation of the 0.1% w/w Fluticasone Propionate Nanosuspension

In an ISO 5 environment, the content of the bottles containing the autoclaved sterile 1% w/w fluticasone propionate nanocrystals of Step 4) were aseptically transferred and pooled into a final compounding vessel.

The weight of the 1% fluticasone propionate nanocrystals slurry transferred in the vessel was recorded (1366.3 g).

The final 0.1% sterile fluticasone propionate nanocrystal suspension was obtained by adding 11774.2 g of the sterile vehicle 3.

The final sterile nanosuspension was stirred for not less than 15 minutes on a stir plate.

The particle size distribution was tested by laser diffraction using a Horiba LA-950S2 PSD analyzer.

The results were the following:
Mean: 0.846 μm
Mode: 0.362 μm
Median: 0.425 μm
$D_{10}$: 0.202 μm
$D_{90}$: 2.219 μm Nanosuspensions according to the invention containing different concentrations of fluticasone propionate form A such as 0.5% w/w, 0.25% w/w, 0.20% w/w, 0.1% w/w, 0.05% w/w, 0.03% w/w, 0.01% w/w and 0.005% w/w were obtained by diluting the de-agglomerated 1% fluticasone propionate nanosuspension of step 4) with aliquots of aqueous vehicle 3 as disclosed in step 6) to obtain the final fluticasone propionate concentration.

Example 3

Evaluation of the Stability of the Nanosuspension of Example 2

The nanosuspension composition prepared in example 2 was subjected to storage stability testing by storing the nanosuspension at three different temperatures and humidity conditions (5° C., 25° C./40% RH; 40° C./25% RH) The resuspendability of the nanosuspension, the content of fluticasone propionate, the particle size distribution and the content of benzalkonium chloride were assessed at 1 month and 3-month time-points.

The results reported in tables 2 and 3 show that the nanosuspension was physically and chemically stable upon manufacture and storage. No change in physical appearance of the nanosuspension upon storage was noticed. The nanosuspension did not show any sign of chemical degradation as the chemical assay of fluticasone propionate was well within the limit of 90%-110% of the label claim upon storage. The related substances and total impurities remained within the specified limits of not more than 4%, upon storage.

TABLE 2

1-month time-point stability data

| | | T = 1 month | | |
|---|---|---|---|---|
| Parameter | T0 n/a | 5° C. | 25° C. 40% RH | 40° C. 25% RH |
| Fluticasone propionate assay | 105.6% | 103.8% | 98.2% | 101.2% |
| Fluticasone Propionate Related substances (total) | 0.0% | 0.25% | 0.10% | 0.11% |
| Resuspendability | n/a | Readily resuspends | Readily resuspends | Readily resuspends |
| BAK content | 99.1% | 98% | 97% | 98% |
| PSD results (μm) | | | | |
| Mean | 0.846 | 0.816 | 0.796 | 0.825 |
| Median | 0.425 | 0.461 | 0.412 | 0.455 |
| Mode | 0.362 | 0.366 | 0.363 | 0.366 |
| $D_{10}$ | 0.202 | 0.213 | 0.200 | 0.212 |
| $D_{90}$ | 2.219 | 1.731 | 1.991 | 1.866 |

TABLE 3

3-month time-point stability data

| | | T = 3 months | | |
|---|---|---|---|---|
| Parameter | T0 n/a | 5° C. | 25° C. 40% RH | 40° C. 25% RH |
| Fluticasone propionate assay | 105.6% | 103% | 104% | 104% |
| FP Related substances (total) | 0.0% | 0.11% | 0.12% | 0.11% |
| Resuspendability | n/a | Resuspends | Resuspends | Resuspends |
| BAK content | 99.1% | 101% | 101% | 97% |
| PSD results (μm) | | | | |
| Mean | 0.846 | 0.830 | 0.830 | 0.770 |
| Median | 0.425 | 0.460 | 0.480 | 0.330 |
| Mode | 0.362 | 0.370 | 0.420 | 0.320 |
| $D_{10}$ | 0.202 | 0.220 | 0.230 | 0.170 |
| $D_{90}$ | 2.219 | 1.980 | 1.890 | 2.250 |

Example 4 (Comparative Example)

The results of this study show that nanosuspensions of fluticasone propionate Form A nanocrystals containing boric acid but no glycerin are not stable and aggregate.

Fluticasone propionate Form A nanocrystals were suspended in a vehicle containing the exact same concentrations of boric acid and of methylcellulose as in the previous Example 2 but it does not contain glycerol.

The compositions of the tested nanosuspensions are reported in Table 4.

TABLE 4

Tested nanosuspensions

| Ingredient | Concentration (% w/w) | | | | |
|---|---|---|---|---|---|
| Fluticasone Propionate | 0.1 | 0.03 | 0.01 | 0.005 | N/A |
| Methylcellulose 4000 cP | 0.5 | 0.5 | 0.5 | 0.5 | 0.5 |
| Polysorbate 80 (Tween 80) | 0.2 | 0.2 | 0.2 | 0.2 | 0.2 |
| Edetate disodium, dihydrate | 0.1 | 0.1 | 0.1 | 0.1 | 0.1 |
| Boric acid | 1.0 | 1.0 | 1.0 | 1.0 | 1.0 |
| Sodium chloride | 0.055 | 0.055 | 0.055 | 0.055 | 0.055 |
| Glycerin | 0 | 0 | 0 | 0 | 0 |
| Benzalkonium chloride | 0.01 | 0.01 | 0.01 | 0.01 | 0.01 |
| Water for Injection | q.s. to 100 | q.s. to 100 | q.s. to 100 | q.s. to 100 | q.s. to 100 |

Preparation of the Fluticasone Propionate Form A Nanocrystal Suspensions

An amount of Fluticasone propionate Form A nanocrystals were suspended in aliquots of vehicle consisting of: 0.50% w/w methylcellulose 4000 cp, 0.2% w/w polysorbate 80, 0.10% w/w edetate disodium dihydrate, 1.0% w/w boric acid; 0.01% w/w benzalkonium chloride and water q.s to 100% w/w (see Table 4), to get the targeted concentrations of fluticasone propionate (see Table 4). Once the nanocrystals were suspended, the suspension was poured into a 500 mL glass beaker for deagglomeration using a high-speed, high-shear Silverson mixing apparatus. The suspension was mixed at 6000 RPM until particle size distribution specifications were met. The particle size distribution and the viscosity of the nanosuspensions were measured.

The nanosuspensions were placed on stability at 40° C., the particle size distribution (PDS) and the viscosity were measured at 2-week time point.

The results reported in Tables 5a and 5b show that over a short period of two weeks only, there was an increase of the mean particle size and of the $D_{90}$, reflecting the formation of aggregates in the nanosuspensions; conversely the stability results reported in Example 3 show that the nanosuspension prepared according to the process of the invention was stable under accelerated conditions up to 3 months.

TABLE 5a

PSD and viscosity assessments

| Time | T0 | 2 weeks |
|---|---|---|
| Formulation containing 0.1% of Fluticasone propionate | | |
| Viscosity in cP | 18.6 | 15.7 |
| Particle Size Distribution results in μm | | |
| Mode | 0.212 | 0.183 |
| Median | 0.245 | 0.261 |
| Mean | 0.382 | 2.575 |

TABLE 5a-continued

PSD and viscosity assessments

| Time | T0 | 2 weeks |
|---|---|---|
| $D_{10}$ | 0.137 | 0.261 |
| $D_{90}$ | 0.754 | 7.571 |
| Formulation containing 0.03% of Fluticasone propionate | | |
| Viscosity in cP | 19.7 | 15.6 |
| Particle Size Distribution results in μm | | |
| Mode | 0.317 | 0.210 |
| Median | 0.319 | 0.291 |
| Mean | 0.437 | 2.128 |
| $D_{10}$ | 0.161 | 0.141 |
| $D_{90}$ | 0.829 | 6.279 |

TABLE 5b

PSD and viscosity assessments

| Time | T0 | 2 weeks |
|---|---|---|
| Formulation containing 0.01% of Fluticasone propionate | | |
| Viscosity in cP | 19.7 | 15.1 |
| Particle Size Distribution results in μm | | |
| Mode | 0.319 | 0.317 |
| Median | 0.336 | 0.467 |
| Mean | 0.463 | 1.808 |
| $D_{10}$ | 0.179 | 0.197 |
| $D_{90}$ | 0.854 | 4.719 |
| Formulation containing 0.005% of Fluticasone propionate | | |
| Viscosity in cP | 19.3 | 16.3 |
| Particle Size Distribution results in μm | | |
| Mode | 0.319 | 0.318 |
| Median | 0.337 | 0.427 |
| Mean | 0.382 | 1.050 |
| $D_{10}$ | 0.179 | 0.190 |
| $D_{90}$ | 0.931 | 2.619 |
| Formulation containing 0.0% of Fluticasone propionate | | |
| Viscosity in cP | 18.6 | 16.6 |

Example 5 (Comparative Example)

The results of this study confirmed that adding the Fluticasone propionate Form A nanocrystals into a vehicle containing the pre-formed boric acid/glycerol complex leads to a residual aggregation which is not observed when the nanosuspension is prepared according to the process of the present invention wherein the glycerol is added to the high speed high, shear mixing de-agglomerated 2% fluticasone propionate nanocrystals slurry (see Example 2-Step 4).

Fluticasone propionate Form A nanocrystals were suspended and de-agglomerated in the vehicle containing the pre-formed boric acid/glycerol complex (boric acid 1.0% w/w/glycerol 0.25% w/w and boric acid 1.0% w/w/glycerol 1.0% w/w) to get a final concentration of Fluticasone propionate of 0.25% w/w.

The compositions of the vehicles of the two tested nanosuspensions are reported in Table 6.

TABLE 6

Tested nanosuspensions

| Ingredient | Concentration (% w/w) | |
|---|---|---|
| Fluticasone Propionate | 0.25 | 0.25 |
| Methylcellulose 4000 cP | 0.5 | 0.5 |
| Tween 80 | 0.2 | 0.2 |
| EDTA disodium, dihydrate | 0.1 | 0.1 |
| Boric acid | 1.0 | 1.0 |
| Sodium chloride | 0.05 | 0.05 |
| Glycerol | 0.25 | 1.0 |
| Benzalkonium chloride | 0.01 | 0.01 |
| Water for Injection | q.s. to 100 | q.s. to 100 |

Preparation of the Fluticasone Propionate Form A Nanocrystal Nanosuspensions

Fluticasone propionate Form A nanocrystals were suspended in the two vehicles reported in Table 6 that contain the pre-formed boric acid/glycerol complex and stirred overnight on a magnetic stir plate, using a stir bar. Once the nanocrystals were suspended, the suspension was poured into a 500 mL glass beaker for de-agglomeration using a high-speed, high-shear, Silverson mixing apparatus. The suspension was mixed at 6000 RPM until particle size distribution specifications were met.

Figure 2:
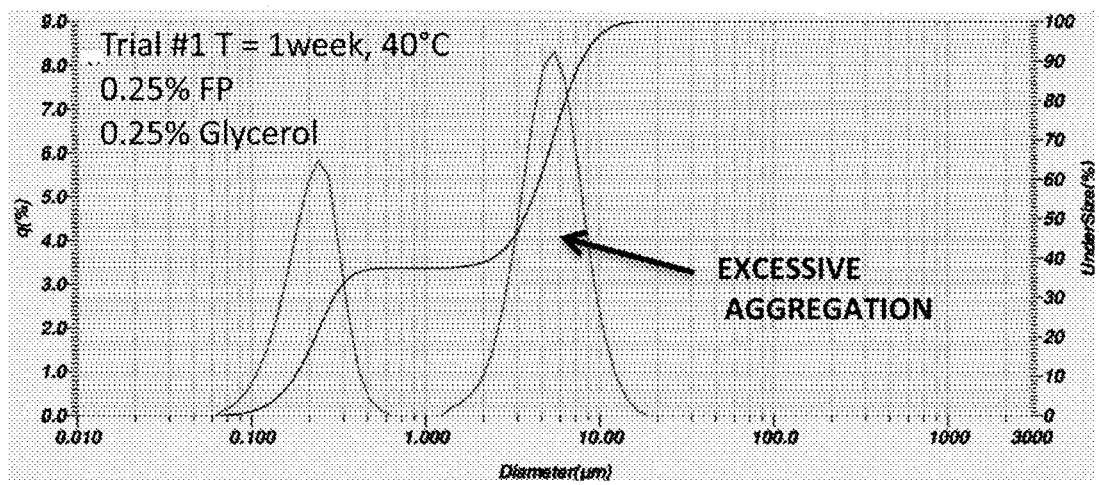
FIG. 2: Particle size distribution graph at T=1 week at 40° C.; 0.25% fluticasone propionate Form A nanocrystals in a vehicle containing a pre-formed 1% w/w boric acid/0.25% w/w glycerol complex (comparative example).
Figure 3:
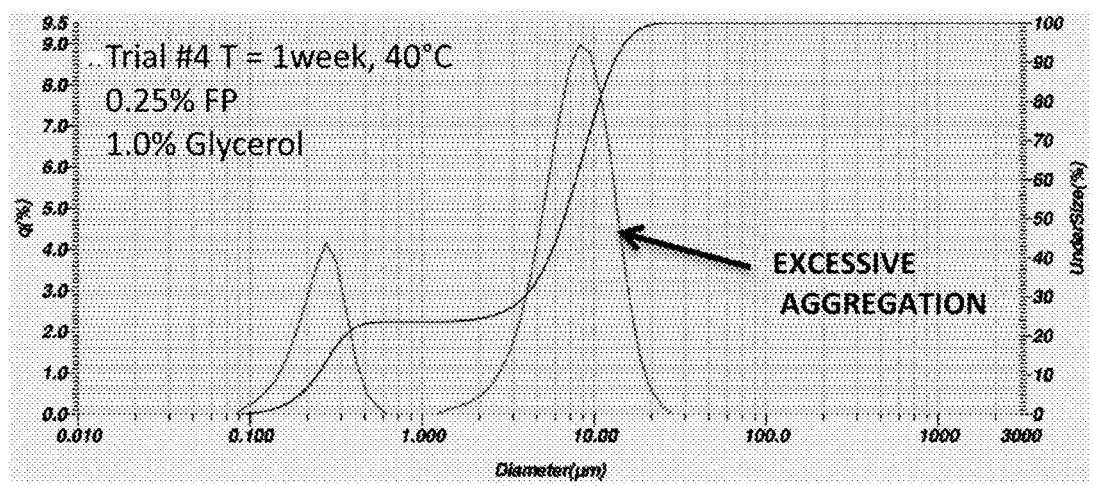
FIG. 3: Particle size distribution graph at T=1 week at 40° C.; 0.25% fluticasone propionate Form A nanocrystals in a vehicle containing a pre-formed 1% w/w boric acid 1% w/w glycerol (comparative example).

The two formulations were placed on stability at 40° C. and the particles size distribution was measured on samples pulled out at 1-week time point. The samples were analyzed shortly after being pulled from the stability chamber. The results show a great deal of aggregation in the samples (see FIGS. 2 and 3).

Figure 4:
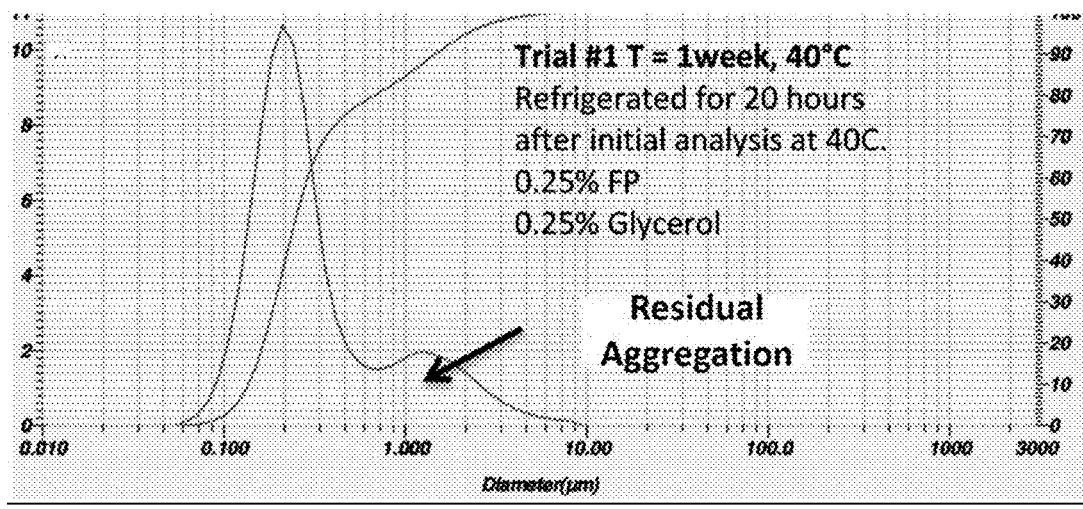
FIG. 4: Particle size distribution graph at T=1 week at 40° C., refrigerated for 20 hours storage at 5° C. after initial analysis at 40° C.; 0.25% w/w fluticasone propionate Form A nanocrystals in a vehicle with 0.25% w/w glycerol (comparative example).

The aggregation was partly reversible when the samples were refrigerated but there still was a substantial residual level of aggregation (see FIG. 4); this thermo-reversible aggregation was related to the decrease of the solubility of the methylcellulose when the temperature increases. It is known that even though methylcellulose solutions are visually clear with no detectable particles in the range of 30-50° C., the polymer chains form loosely-associated clusters that grow in size as the temperature increases. These clusters are likely responsible for part of the aggregation of the nanocrystals at 40° C.

As reported above, the results of this study demonstrated that glycerol acts as a stabilizer by forming a complex with the boric acid that prevents the aggregation of the isolated nanocrystals. If the nanosuspension is prepared by suspending the nanocrystals in the vehicle that contains the pre-formed complex boric acid/glycerol, the stabilizing effect of the complex is reduced.

Example 6

In Vitro Dissolution Test

The dissolution rate of the Fluticasone propionate form A nanocrystals of the nanosuspension of the invention was assessed and compared to the dissolution rate of a standard Fluticasone propionate form 1 micronized material (reference sample).

Dissolution profiles of nanocrystals of Fluticasone propionate form A of two nanosuspensions of the invention and of Fluticasone propionate form 1 micronized were performed using a dissolution method.

The particle size of the Fluticasone propionate Form A nanocrystals is 0.434 μm (D50-median) and the particle size of the Fluticasone propionate form 1 micronized material is 4.64 μm (D50-median).

The study was performed using a compartment diffusion analysis through a dialysis membrane and sink condition. The sink condition was achieved through the use of a receptor fluid containing 30 mM phosphate buffer, pH 7.4 with 5% HPβCD cyclodextrins and also by a complete replacement of the buffer every 24 hours to stay below the saturation point. The saturation point was estimated to be 5 μg/g under those experimental conditions and the measurements performed as well as the buffer replacement have shown a maximum concentration of 1.5 μg/g. The study was conducted at a temperature of 37° C. The details of the dissolution test method are provided below:

A 5-fold dilution with the formulation vehicle (placebo solution containing all the formulation excipients including the surfactants) of two 0.1% w/w Fluticasone propionate form A nanosuspensions was conducted to obtain a final concentration of 0.02% w/w Fluticasone propionate inside the dialysis device.

Fluticasone propionate form 1 micronized was suspended in the same phosphate buffer used in the receiving compartment of the dialysis system.

Fluticasone propionate release was carried at 1-2 RPM.

Sampling aliquots of 1 mL were withdrawn at pre-determined time intervals (1, 3, 5, 20, 24, 48, 72 hours), and replaced with an equal volume of dissolution medium to maintain a constant total volume of 39 ml in the 50 ml tube.

These aliquots were immediately centrifuged and the measurements were performed by HPLC The results reported in tables 7-9 show that the dissolution profiles of the nanocrystals of Fluticasone propionate form A and of the Fluticasone propionate form 1 micronized material were similar despite that the two test samples and the reference sample have different particle size. More specifically, the particle size of Fluticasone propionate Form A nanocrystals is ten-fold smaller ($D_{50}$=0.434 μm) than the particle size of the micronized Fluticasone propionate form 1 ($D_{50}$=4.64 μm).

Since, the solubility of a compound is often intrinsically related to the particle size, as a particle becomes smaller, the surface area to volume ratio increases leading to greater interaction with the solvent which causes an increase in solubility, the results of this study show the unique property of the ophthalmic aqueous fluticasone propionate Form A nanocrystals of the invention, namely on one hand the small particle size (nanoparticles) improves the comfort and the tolerability of the ophthalmic formulation, on the other hand the slow dissolution rate of the fluticasone propionate active principle allows to avoid a fast and high absorption of fluticasone propionate correlated to the unwanted side-effects associated with the systemic absorption of the steroid.

TABLE 7

Dissolution test of Fluticasone propionate form A nanocrystals

| Time point (h) | % Dissolution | | | | | |
|---|---|---|---|---|---|---|
| | Tube #1 | Tube #2 | Tube #3 | Average % | St. Dev. | RSD |
| 1 | 0.0% | 0.0% | 0.0% | 0.0% | 0.0% | |
| 3 | 0.2% | 1.4% | 0.7% | 0.8% | 0.6% | 73.2% |
| 5 | 1.3% | 2.8% | 2.4% | 2.2% | 0.8% | 35.6% |
| 19 | 14.5% | 20.4% | 18.7% | 17.8% | 3.0% | 16.9% |
| 24 | 17.5% | 24.0% | 22.4% | 21.3% | 3.4% | 15.9% |
| 48 | 38.7% | 51.4% | 48.6% | 46.2% | 6.7% | 14.4% |
| 72 | 59.6% | 78.1% | 74.0% | 70.5% | 9.7% | 13.7% |

TABLE 8

Dissolution test of Fluticasone propionate form A nanocrystals

| Time point (h) | % Dissolution | | | | | |
|---|---|---|---|---|---|---|
| | Tube #1 | Tube #2 | Tube #3 | Average % | St. Dev. | RSD |
| 1 | 0.0% | 0.0% | 0.0% | 0.0% | 0.0% | |
| 3 | 0.6% | 0.5% | 0.8% | 0.7% | 0.2% | 26.7% |
| 5 | 2.4% | 2.0% | 2.6% | 2.3% | 0.3% | 11.2% |
| 19 | 19.0% | 18.2% | 19.7% | 19.0% | 0.8% | 4.1% |
| 24 | 22.4% | 21.5% | 23.2% | 22.4% | 0.9% | 3.8% |
| 48 | 49.1% | 45.6% | 50.9% | 48.5% | 2.7% | 5.6% |
| 72 | 75.1% | 69.1% | 77.7% | 73.9% | 4.4% | 6.0% |

TABLE 9

Dissolution test of Micronized Fluticasone propionate form 1

| Time point (h) | % Dissolution | | | | | |
|---|---|---|---|---|---|---|
| | Tube #1 | Tube #2 | Tube #3 | Average % | St. Dev. | RSD |
| 1 | 0.0% | 0.0% | 0.0% | 0.0% | 0.0% | |
| 3 | 0.8% | 0.5% | 0.9% | 0.7% | 0.2% | 31.2% |
| 5 | 2.9% | 1.9% | 3.0% | 2.6% | 0.6% | 23.1% |
| 19 | 20.9% | 17.1% | 20.3% | 19.4% | 2.1% | 10.7% |
| 24 | 24.2% | 20.2% | 23.5% | 22.6% | 2.2% | 9.5% |
| 48 | 51.1% | 44.0% | 50.6% | 48.6% | 4.0% | 8.2% |
| 72 | 77.4% | 66.7% | 76.2% | 73.4% | 5.9% | 8.0% |

Example 7

14-Day Repeated Dose Study of Topical Ophthalmic Aqueous Fluticasone Propionate Form A Nanocrystals Suspensions in Beagle Dogs The purpose of this study was to evaluate the toxicokinetic of fluticasone propionate Form A nanosuspensions of the invention (see Table 10 below) administered via topical application directly to the rim (margin) of upper and lower eyelids of both eyes of Beagle dogs.

TABLE 10

Test formulations composition

| Ingredient | % (w/w) | % (w/w) | % (w/w) | % (w/w) |
|---|---|---|---|---|
| Fluticasone Propionate | 0.00 | 0.005 | 0.03 | 0.1 |
| Methylcellulose 4000 cP | 0.50 | 0.50 | 0.50 | 0.50 |
| Tween 80 | 0.20 | 0.20 | 0.20 | 0.20 |
| Edetate disodium, dihydrate | 0.10 | 0.10 | 0.10 | 0.10 |
| Boric acid | 1.00 | 1.00 | 1.00 | 1.00 |
| Sodium chloride | 0.055 | 0.055 | 0.055 | 0.055 |
| Glycerol | 0.90 | 0.90 | 0.90 | 0.90 |
| Benzalkonium chloride | 0.01 | 0.01 | 0.01 | 0.01 |
| Water for Injection | q.s. to 100 | q.s. to 100 | q.s. to 100 | q.s. to 100 |

Methods

Fifty naïve Beagle dogs (25 males and 25 females), approximately 5-6 months old and weighing 5.7 to 8.8 kg for males and females at the outset of the study were assigned to treatment groups (groups 1-4) and to vehicle group.

Male and female Beagle dogs were dosed with fluticasone propionate at 1.6, 9.6, and 32 µg/day (bilateral QD topical application) or at 64 µg/day (bilateral BID topical application) via eye lid applicator directly to the upper and lower eyelids of both eyes once or twice daily (minimum of 6 hours between doses) for 14 consecutive days.

Blood for toxicokinetic evaluation was collected from all animals at selected time points on Days 1 and 14.

Ophthalmology examinations were performed prior to treatment initiation, during the first and second weeks of dosing and during the last week of recovery. Eyes were scored once daily according to the modified Draize scale.

The reversibility of the effects of Fluticasone Propionate nanosuspension was assessed with a 14-day recovery period.

Results and Conclusions

The group mean plasma toxicokinetic parameters are summarized in Table 11 below.

The results show that exposure to fluticasone propionate was dose-dependent increasing with increasing doses. There was no clear evidence of accumulation in male and female animals. There were no discernable gender-related differences in exposure. Systemic exposure (AUC) at the lowest observed adverse effect level associated with corticosteroid-related findings in a 14-day inhalation toxicity study in dogs was 14- and 9-times higher than that observed at the ocular dose of 0.1% QD and BID, in the 14-day topical ocular toxicity study in dogs (Advair-Diskuss-NDA-021077).

There was no evidence of local or systemic toxicity.

TABLE 11

Plasma Toxicokinetic Parameters of Fluticasone Propionate following topical ocular eyelid margin administration

| Study Day | Ocular Treatment | Dose (µg/day) | Tmax (h) | Cmax (pg/mL) | $AUC_0$-24h (pg.h/mL) |
|---|---|---|---|---|---|
| 1 | 0.005% QD | 1.6 | 0.5 | 32.4 ± 26.4 | 25.7 ± 18.5 |
| | 0.03% QD | 9.6 | 0.5 | 79.8 ± 70.0 | 101 ± 102 |
| | 0.1% QD | 32 | 0.5 | 250 ± 219 | 482 ± 407 |
| | 0.1% BID | 64 | 6.5 | 304 ± 178 | 914 ± 413 |
| 14 | 0.005% QD | 1.6 | 0.75 | 28.1 ± 26.6 | 56.8 ± 65.0 |
| | 0.03% QD | 9.6 | 0.5 | 60.8 ± 48.7 | 191 ± 335 |
| | 0.1% QD | 32 | 0.5 | 130 ± 155 | 481 ± 361 |
| | 0.1% BID | 64 | 0.5 | 126 ± 93.6 | 760 ± 188 |

Example 8

Evaluation of Efficacy and Safety of Fluticasone Propionate Form A Nanosuspension for the Treatment of Acute Exacerbations of Blepharitis The objective of this study was to compare the efficacy and safety of an aqueous ophthalmic formulation of Fluticasone propionate form A nanosuspension of the invention versus placebo in reducing signs and symptoms in subjects with blepharitis.

Test Formulation (hereafter FP-Form A-NS)

0.1% w/w fluticasone propionate Form A nanocrystals (mean particle size from 100 nm to 1000 nm) 0.50% w/w methylcellulose 4000 cp, 0.2% w/w polysorbate 80, 0.10% w/w edetate disodium dihydrate, 1.0% w/w boric acid, 0.9% w/w glycerin, 0.01% w/w benzalkonium chloride, 0.055% w/w sodium chloride, hydrochloric acid (1N) and/or sodium hydroxide (1N) as adjusting agents in an amount sufficient for pH from 7.3-7.5, and water q.s. to 100% w/w.

Placebo Formulation 0.50% w/w methylcellulose 4000 cp, 0.2% w/w polysorbate 80, 0.10% w/w edetate disodium dihydrate, 1.0% w/w boric acid, 0.9% w/w glycerin, 0.01% w/w benzalkonium chloride, 0.055% w/w sodium chloride, hydrochloric acid (1N) and/or sodium hydroxide (1N) as adjusting agents in an amount sufficient for pH from 7.3-7.5, and water q.s. to 100% w/w.

Study Design

This was a Phase 2 multi-center, randomized, double-masked, placebo-controlled study evaluating the safety and efficacy of fluticasone propionate Form A nanosuspension 0.1% once a day for the treatment of the signs and symptoms of blepharitis.

The target population in this study was adult men and women with a documented history of blepharitis who were experiencing an acute blepharitis exacerbation defined as a minimum score of '1' (on a 4-point scale) for each of Eyelid Margin Redness, Eyelid Debris, and Eyelid Discomfort in both eyes at the Screening and Baseline Visits. A total of 15 subjects were included in the study. Subject ages were between 55 and 80 years old, with an average age of 70.8 years.

Fifteen patients have been randomized at three clinical sites across the U.S. Ten patients received FP-Form A-NS and 5 patients received placebo, once a day in the evening for both eyes.

Study visits were as follows: Screening (Day −7 to −3), Baseline/Day 1, Day 4 (±1 day), Day 8 (±1 day), Day 11 (±1 day), Day 14 (−1 day; last day of treatment), and Day 28/Exit (±2 days; follow up visit).

Test nanosuspension (16 µg of fluticasone propionate per eye) or placebo were applied once a day in the evening. Study drug was self-administered by the subjects.

Evaluation of the Efficacy and Safety of the Fluticasone Propionate Form A Nanosuspension Efficacy and safety of fluticasone propionate form A nanosuspension (FP-Form A-NS) were compared with placebo at each post-dose visit during the study. In addition of signs and symptoms of blepharitis, this study evaluated signs and symptoms characteristic of dry eye disease, also commonly observed in subjects with blepharitis.

Efficacy

The results of the study reported in Tables 12 and 13 demonstrated that fluticasone propionate form A nanosuspension treatment consistently improved the signs and symptoms in subjects with blepharitis and that subjects treated with fluticasone propionate form A nanosuspension showed a decrease in the composite score of debris, redness and discomfort from baseline and versus subjects treated with placebo.

The results presented in Tables 12 and 13 are related to signs and symptoms of blepharitis in the study eye evaluated after 14 days of treatment and conducted prior to daily eyelid scrub procedures.

The following dry eye symptoms were also evaluated with Visual Analog Scales (VAS) by the subjects: eye dryness, burning-stinging, foreign body sensation, itching, photophobia, pain and blurred vision. The composite VAS score (the average of individual scores of these symptoms) reported in Table 14 demonstrated that fluticasone propionate Form A nanosuspension treatment was efficacious in reducing dry eye symptoms with respect to placebo.

Safety

The treatment with fluticasone propionate Form A nanosuspension of the invention was very well tolerated, all patients completed the treatment. There were no Serious Adverse Events (SAEs) and in particular, no clinically relevant changes in subject's intraocular pressure were observed during treatment or up to two weeks after treatment discontinuation.

The results of this study demonstrate that fluticasone propionate Form A nanosuspension of the invention is able to reduce both signs and symptoms of blepharitis and dry eye and that the treatment and application method have a safe tolerability profile.

TABLE 12

Signs and symptoms of blepharitis at Day 14 of treatment with fluticasone propionate form A nanosuspension of the invention (FP-Form A-NS) versus placebo

| | Placebo | FP-Form A-NS |
|---|---|---|
| Eyelid Margin Redness | | |
| Baseline (SD) | 1.6 (0.89) | 1.5 (0.53) |
| Day 14 (SD) | 1.2 (0.45) | 0.9 (0.74) |
| Change from Baseline (SD) | −0.4 (0.55) | −0.6 (0.52) |
| p values | 0.1778 | 0.0051 |
| FP-Form A-NS vs. Placebo (95% CI) | −0.2 (−0.8, 0.4) p = 0.5000 | |
| Eyelid Debris | | |
| Baseline (SD) | 1.8 (0.45) | 1.6 (0.70) |
| Day 14 (SD) | 1.2 (0.45) | 0.7 (0.67) |
| Change from Baseline (SD) | −0.6 (0.55) | −0.9 (0.88) |
| p value | 0.0705 | 0.0100 |
| FP-Form A-NS vs. Placebo (95% CI) | −0.3 (−1.2, −0.3) p = 0.5000 | |
| Eyelid Discomfort | | |
| Baseline (SD) | 1.8 (0.45) | 1.6 (0.52) |
| Day 14 (SD) | 1.4 (1.14) | 0.9 (0.88) |
| Change from Baseline (SD) | −0.4 (0.89) | −0.7 (1.16) |
| p values | 0.3739 | 0.0886 |
| FP-Form A-NS vs. Placebo (95% CI) | −0.3 (−1.6, 1.0) p = 0.6221 | |

TABLE 13

Composite score of Eyelid Margin Redness, Eyelid Debris, and Eyelid Discomfort at 14 Day of treatment with fluticasone propionate form A nanosuspension of the invention (FP-Form A-NS) versus placebo

| Composite Eyelid Debris, Redness & Discomfort | Placebo | FP-Form A-NS |
|---|---|---|
| Baseline (SD) | 5.2 (1.30) | 4.7 (0.82) |
| Day 14 (SD) | 3.8 (1.48) | 2.5 (1.90) |
| Change from Baseline (SD) | −1.4 (0.55) | −2.2 (1.62) |
| p values | 0.0046 | 0.0020 |
| FP-Form A-NS vs. Placebo (95% CI) | −0.8 (−2.4, 0.8) p = 0.3095 | |

TABLE 14

Composite VAS score of dry eye symptoms: eye dryness, burning-stinging, foreign body sensation, itching, photophobia, pain and blurred vision, at 14 Day of treatment with fluticasone propionate form A nanosuspension of the invention (FP-Form A-NS) versus placebo

| Composite VAS score | Placebo | FP-Form A-NS |
|---|---|---|
| Baseline (SD) | 41.8 (29.72) | 44.8 (17.81) |
| Day 14 (SD) | 32.9 (27.17) | 26.1 (18.05) |
| Change from Baseline (SD) | −8.9 (9.37) | −18.8 (19.73) |
| p values | 0.1005 | 0.0147 |
| FP-Form A-NS vs. Placebo (95% CI) | −9.9 (−30.2, 10.5) p = 0.3142 | |

Example 9

Evaluation of the Stability of the Nanosuspension of Example 2

The nanosuspension composition prepared in example 2 was subjected to storage stability testing by storing the nanosuspension at three different temperatures and humidity conditions (5° C., 25° C./40% RH; 40° C./25% RH) The resuspendability of the nanosuspension, the content of fluticasone propionate, the particle size distribution and the content of benzalkonium chloride were assessed at 1 month and 3-month time-points (see results reported in Example 3 and Tables 2 and 3), at 5-month time point at 40° C. (Table 15) up to 12 months at 5° C. and 25° C. (Table 16).

The results reported in tables 15 and 16 show that the nanosuspension was physically and chemically stable upon storage. No change in physical appearance of the nanosuspension upon storage was noticed. The nanosuspension did not show any sign of chemical degradation as the chemical assay of fluticasone propionate was well within the limit of 90%-110% of the label claim upon storage. The related substances and total impurities remained within the specified limits of not more than 4%, upon storage.

Particle size distribution was analyzed using a Horiba LA-950 instrument.

TABLE 15

5-month time-point stability data

| Parameter | T0<br>n/a | T = 5-month<br>40° C.<br>25% RH |
|---|---|---|
| Fluticasone propionate assay | 105.6% | 104% |
| FP Related substances (total) | 0.0% | 0.11% |
| Resuspendability | n/a | Resuspends |
| BAK content | 99.1% | 103% |
| PSD results (μm) | | |
| Mean | 0.846 | 0.82 |
| Median | 0.425 | 0.50 |
| Mode | 0.362 | 0.42 |
| $D_{10}$ | 0.202 | 0.23 |
| $D_{90}$ | 2.219 | 1.84 |

TABLE 16

12-month time-point stability data

| Parameter | T0<br>n/a | T = 12-month | |
|---|---|---|---|
| | | 5° C. | 25° C.<br>40% RH |
| Fluticasone propionate assay | 105.6% | 105% | 107% |
| FP Related substances (total) | 0.0% | 0.61% | 0.48% |
| Resuspendability | n/a | Resuspends | Resuspends |
| BAK content | 99.1% | 101% | 96% |
| PSD results (μm) | | | |
| Mean | 0.846 | 0.90 | 0.86 |
| Median | 0.425 | 0.45 | 0.45 |
| Mode | 0.362 | 0.36 | 0.36 |
| $D_{10}$ | 0.202 | 0.21 | 0.21 |
| $D_{90}$ | 2.219 | 2.16 | 2.08 |

We claim:

1. A process for the preparation of sterile topical ophthalmic aqueous nanosuspensions containing fluticasone propionate Form A nanocrystals having a mean particle size from 100 nm to 1000 nm and a targeted concentration of fluticasone propionate from 0.001% w/w to 1% w/w, said process comprising:
   a) preparing an aqueous vehicle 1 containing: 0.5% w/w methylcellulose 4000 cp, 1.0% w/w boric acid, 0.1% w/w edetate disodium dihydrate, 0.055% w/w sodium chloride, 0.01% w/w benzalkonium chloride, 0.2% w/w polysorbate 80, hydrochloric acid 1N and/or sodium hydroxide 1N to adjust the pH at 7.3-7.5 and water to 100% w/w;
   b) mixing an amount of fluticasone propionate Form A nanocrystals having a mean particle size from 100 nm to 1000 nm with an amount of aqueous vehicle 1 to obtain a slurry containing a concentration of fluticasone propionate of 2% w/w;
   c) applying high-shear, high-speed mixing to the slurry of step b) for at least 10 minutes;
   d) preparing an aqueous vehicle 2 containing: 1.8% w/w glycerin, 0.5% w/w methylcellulose 4000 cp, 1.0% w/w boric acid, 0.1% w/w edetate disodium dihydrate, 0.055% w/w sodium chloride, 0.01% w/w benzalkonium chloride, 0.2% w/w polysorbate 80, hydrochloric acid 1N and/or sodium hydroxide 1N to adjust the pH at 7.3-7.5 and water q.s. to 100% w/w;
   e) adding an aliquot of the aqueous vehicle 2 to the slurry of step c) to obtain a concentration of fluticasone propionate of about 1% w/w;
   f) applying high-shear, high-speed mixing to the slurry of step e) to obtain the targeted mean particle size;
   g) sterilizing the nanosuspension of step f) by autoclaving;
   h) preparing an aqueous vehicle 3 containing: 0.9% w/w glycerin, 0.5% w/w methylcellulose 4000 cp, 1.0% w/w boric acid, 0.1% w/w edetate disodium dihydrate, 0.055% w/w sodium chloride, 0.01% w/w benzalkonium chloride, 0.2% w/w polysorbate 80, hydrochloric acid 1N and/or sodium hydroxide 1N to adjust the pH at 7.3-7.5 and water to 100% w/w; and sterilizing the aqueous vehicle 3 by filtration;
   i) aseptically adding an aliquot of the sterile aqueous vehicle 3 to the sterilized nanosuspension of step g) to prepare a final sterile topical ophthalmic aqueous nanosuspension containing the targeted concentration of fluticasone propionate nanocrystals Form A;
   wherein the nanocrystals of fluticasone propionate Form A have a X-ray powder diffraction pattern of said nanocrystals comprising peaks at about 7.8, 15.7, 20.8, 23.7, 24.5, and 32.5 degrees 2Θ, further comprising peaks at about 9.9, 13.0, 14.6, 16.0, 16.9, 18.1, and 34.3 degrees 2Θ, and wherein the nanocrystals are nanoplates having the [001] crystallographic axis normal to the surfaces that define the thickness of the nanoplates.

2. The process according to claim 1 wherein the concentration of fluticasone propionate in the final sterile topical ophthalmic aqueous nanosuspension is from 0.001% to 0.5% w/w.

3. The process according to claim 1 wherein the concentration of fluticasone propionate in the final sterile topical ophthalmic aqueous nanosuspension is 0.5% w/w, 0.25% w/w, 0.2% w/w, 0.1% w/w, 0.05% w/w, 0.03% w/w, 0.01% w/w or 0.005% w/w.

4. The process according to claim 1 wherein the high-shear, high-speed mixing of steps c) and f) is performed at 6000 RPM.

5. The process according to claim 4 wherein in step f) the high-shear, high-speed mixing is applied for at least 10 minutes.

6. The process according to claim 1 wherein the aqueous vehicles 1 and 2 are filtered through 0.2 µm filter before their use.

7. The process according to claim 1 wherein the sterilization of step g) is performed by autoclaving the nanosuspension of step f) at about 122° C. for about 40 minutes.

8. A process for the preparation of sterile topical ophthalmic aqueous nanosuspensions containing fluticasone propionate Form A nanocrystals having a mean particle size from 100 nm to 1000 nm and a final concentration of fluticasone propionate from 0.001% w/w to 1% w/w, said process comprising:

a-1) sterilizing fluticasone propionate Form A nanocrystals having a mean particle size from 100 nm to 1000 nm;
   b-1) preparing an aqueous vehicle 1 containing: 0.5% w/w methylcellulose 4000 cp, 1.0% w/w boric acid, 0.1% w/w edetate disodium dihydrate, 0.055% w/w sodium chloride, 0.01% w/w benzalkonium chloride, 0.2% w/w polysorbate 80, hydrochloric acid 1N and/or sodium hydroxide 1N to adjust the pH at 7.3-7.5 and water q.s. to 100% w/w; and sterilizing said aqueous vehicle 1 by filtration;
   c-1) aseptically mixing an amount of sterilized fluticasone propionate nanocrystals form A with an amount of the sterilized aqueous vehicle 1 to obtain a slurry containing a concentration of fluticasone propionate of 2% w/w;
   d-1) applying high-shear, high-speed mixing to the slurry of step c-1) for at least 10 minutes;
   e-1) preparing an aqueous vehicle 2 containing: 1.8% w/w glycerin, 0.5% w/w methylcellulose 4000 cp, 1.0% w/w boric acid, 0.1% w/w edetate disodium dihydrate, 0.055% w/w sodium chloride, 0.01% w/w benzalkonium chloride, 0.2% w/w polysorbate 80, hydrochloric acid 1N/sodium hydroxide 1N to adjust the pH at 7.3-7.5 and water q.s. to 100% w/w; and sterilizing said aqueous vehicle 2 by filtration;
   f-1) aseptically adding an aliquot of the sterilized aqueous vehicle 2 to the slurry of step d-1) to obtain a concentration of fluticasone propionate of about 1% w/w;
   g-1) applying high-shear, high-speed mixing to the slurry of step f-1) to obtain the targeted mean particle size;
   h-1) preparing an aqueous vehicle 3 containing: 0.9% w/w glycerin, 0.5% w/w methylcellulose 4000 cp, 1.0% w/w boric acid, 0.1% w/w edetate disodium dihydrate, 0.055% w/w sodium chloride, 0.01% w/w benzalkonium chloride, 0.2% w/w polysorbate 80, hydrochloric acid 1N and/or sodium hydroxide 1N to adjust the pH at 7.3-7.5 and water to 100% w/w; and sterilizing said aqueous vehicle 3 by filtration;
   i-1) aseptically adding an aliquot of the sterilized aqueous vehicle 3 to the nanosuspension of step g-1) to prepare a sterile topical ophthalmic aqueous nanosuspension containing the final concentration of fluticasone propionate nanocrystals Form A;
   wherein the nanocrystals of fluticasone propionate Form A have a X-ray powder diffraction pattern comprising peaks at about 7.8, 15.7, 20.8, 23.7, 24.5, and 32.5 degrees 2$\Theta$, further comprising peaks at about 9.9, 13.0, 14.6, 16.0, 16.9, 18.1, and 34.3 degrees 2$\Theta$, and wherein the nanocrystals are nanoplates having the [001] crystallographic axis normal to the surfaces that define the thickness of the nanoplates.

9. The process according to claim 8 wherein the final concentration of fluticasone propionate in the sterile topical ophthalmic aqueous nanosuspension is from 0.001% to 0.5% w/w.

10. The process according to claim 8 wherein the final concentration of fluticasone propionate in the sterile topical ophthalmic aqueous nanosuspension is 0.5% w/w, 0.25% w/w, 0.2% w/w, 0.1% w/w, 0.05% w/w, 0.03% w/w, 0.01% w/w or 0.005% w/w.

11. The process according to claim 8 wherein in step a-1) the fluticasone propionate Form A nanocrystals are sterilized by autoclaving a suspension of fluticasone propionate Form A nanocrystals in water for injection having a concentration of fluticasone propionate between 2% to 20% w/w.

12. The process according to claim 11 wherein the suspension of fluticasone propionate Form A nanocrystals in water is autoclaved at about 122° C. for about 30 minutes.

13. The process according to claim 8 wherein in step d-1) and step g-1) the high-shear, high-speed mixing is performed at 6000 RPM.

14. The process according to claim 13 wherein in step g-1) the high-shear, high-speed mixing is applied for at least 10 minutes.

15. The process according to claim 1 wherein fluticasone propionate nanocrystals form A are prepared according to the following steps:

1) preparing a phase I solution comprising 0.45% w/w fluticasone propionate polymorph 1, 23.2% w/w polyethylene glycol 400 (PEG 400), 68.8% w/w polypropylene glycol 400 (PPG 400), 7.6% w/w polysorbate 80; and filtering the phase I solution through a 0.8/0.2 µm Polyethersulfone (PES) filter;
   2) preparing a phase II solution comprising 0.01% w/w benzalkonium chloride, 0.40% (w/w) methyl cellulose 15 cP, 0.1% w/w polyethylene glycol 40 stearate (PEG-40 stearate), citrate buffer to pH 3.4 to 3.8 and water q.s. to 100% w/w; and filtering the phase II solution through the 0.8/0.2 µm Polyethersulfone (PES) filter;
   3) cooling the filtered phase I and phase II solutions to a temperature from 0 to 4° C.;
   4) mixing the phase I and the phase II solutions in a reactor equipped with ultrasonic transducer to obtain a phase III suspension of nanocrystals, wherein:
      the phase I solution and the phase II solution are pumped continuously into the reactor at flow rates of 600 ml/min (phase I solution) and 2400 ml/min (phase II solution) respectively to obtain a phase III suspension;
      the volumes ratio phase I and phase II is 1:4;
      the sonication is applied during the mixing with an output power of 60%;
      the average temperature of phase III suspension is about 11° C.; and
   5) low shear mixing the phase III suspension of step 4) at sufficient speed to create a vortex, at room temperature for a minimum of 30 minutes in absence of sonication;
   6) annealing the phase III suspension at 40° C. over a period of time not less than 16 hours;
   7) preparing a buffer solution comprising 0.2% w/w polyethylene glycol 40 stearate (PEG-40 stearate), 0.2% w/w polysorbate 80, 0.001% w/w benzalkonium chloride, 0.05% w/w sodium phosphate monobasic monohydrate, 0.02% w/w sodium phosphate dibasic dihydrate and water q.s. to 100% w/w, having a pH 6.3±0.2; and filtering the buffer solution through the 0.8/0.2 µm Polyethersulfone (PES) filter;

8) diluting the phase III suspension of step 6) with the filtered buffer solution wherein the volumes ratio buffer solution and phase III is 1:1;
9) centrifuging the diluted phase III suspension to recover the fluticasone propionate nanocrystals Form A and washing the recovered nanocrystals;
10) washing the collected nanocrystals with water for injection.

16. An ophthalmic aqueous nanosuspension administrable topically onto eyelids, eyelashes or eyelid margin consisting of:
    (a) 0.001% to 1% w/w fluticasone propionate Form A nanocrystals;
    (b) 0.50% w/w methylcellulose 4000 cp;
    (c) 0.2% w/w polysorbate 80;
    (d) 0.10% w/w edetate disodium dihydrate;
    (e) 1.0% w/w boric acid;
    (f) 0.9% w/w glycerin;
    (g) 0.01% w/w benzalkonium chloride;
    (h) 0.055% w/w sodium chloride;
    (i) hydrochloric acid 1N and/or sodium hydroxide 1N as adjusting agents in an amount sufficient to pH 7.3-7.5; and
    (j) water q.s. to 100% w/w,
wherein said nanocrystals of fluticasone propionate Form A have a mean particle size from 100 nm to 1000 nm and a X-ray powder diffraction pattern comprising peaks at about 7.8, 15.7, 20.8, 23.7, 24.5, and 32.5 degrees 2Θ, further comprising peaks at about 9.9, 13.0, 14.6, 16.0, 16.9, 18.1, and 34.3 degrees 2Θ, and wherein the nanocrystals are nanoplates having the [001] crystallographic axis normal to the surfaces that define the thickness of the nanoplates, wherein said ophthalmic aqueous nanosuspension contains a boric acid/glycerol complex.

17. The ophthalmic aqueous nanosuspension according to claim 16 wherein the concentration of fluticasone propionate is from 0.001% to 0.5% w/w.

18. The ophthalmic aqueous nanosuspension according to claim 16 wherein the concentration of fluticasone propionate is 0.5% w/w, 0.25% w/w, 0.2% w/w, 0.1% w/w, 0.05% w/w, 0.03% w/w, 0.01% w/w or 0.005% w/w.

19. The ophthalmic aqueous nanosuspension according to claim 16 wherein the concentration of fluticasone propionate is 0.2% w/w or 0.1% w/w or 0.05% w/w.

20. A method of treating blepharitis, posterior blepharitis, Meibomian gland dysfunction or dry eye disease comprising topically applying an effective amount of the ophthalmic aqueous nanosuspension according to claim 16 to eyelids, eyelashes or eyelid margin of a subject in need thereof.

21. A method of reducing the symptoms and/or clinical signs associated with blepharitis, posterior blepharitis, Meibomian gland dysfunction or dry eye disease comprising topically applying an effective amount of the ophthalmic aqueous nanosuspension according to claim 16 to eyelids, eyelashes or eyelid margin of a subject in need thereof.

22. The method according to claim 20, wherein the ophthalmic aqueous nanosuspension comprises:
    (a) 0.1% w/w fluticasone propionate Form A nanocrystals;
    (b) 0.50% w/w methylcellulose 4000 cp;
    (c) 0.2% w/w polysorbate 80;
    (d) 0.10% w/w edetate disodium dihydrate;
    (e) 1.0% w/w boric acid;
    (f) 0.9% w/w glycerin;
    (g) 0.01% w/w benzalkonium chloride;
    (h) 0.055% w/w sodium chloride;
    (i) hydrochloric acid 1N and/or sodium hydroxide 1N as adjusting agents in an amount sufficient to pH 7.3-7.5; and (j) water q.s. to 100% w/w,
    wherein said nanocrystals of fluticasone propionate Form A have a mean particle size from 100 nm to 1000 nm and a X-ray powder diffraction pattern comprising peaks at about 7.8, 15.7, 20.8, 23.7, 24.5, and 32.5 degrees 2Θ, further comprising peaks at about 9.9, 13.0, 14.6, 16.0, 16.9, 18.1, and 34.3 degrees 2Θ, and wherein the nanocrystals are nanoplates having the [001] crystallographic axis normal to the surfaces that define the thickness of the nanoplates.

23. The method according to claim 20, wherein the method comprises topically applying an effective amount of the ophthalmic aqueous nanosuspension at least once a day for at least two weeks to eyelids, eyelashes or eyelid margin of a subject in need thereof.

24. The method according to claim 21, wherein the ophthalmic aqueous nanosuspension comprises:
    (a) 0.1% w/w fluticasone propionate Form A nanocrystals;
    (b) 0.50% w/w methylcellulose 4000 cp;
    (c) 0.2% w/w polysorbate 80;
    (d) 0.10% w/w edetate disodium dihydrate;
    (e) 1.0% w/w boric acid;
    (f) 0.9% w/w glycerin;
    (g) 0.01% w/w benzalkonium chloride;
    (h) 0.055% w/w sodium chloride;
    (i) hydrochloric acid 1N and/or sodium hydroxide 1N as adjusting agents in an amount sufficient to pH 7.3-7.5; and (j) water q.s. to 100% w/w,
    wherein said nanocrystals of fluticasone propionate Form A have a mean particle size from 100 nm to 1000 nm and a X-ray powder diffraction pattern comprising peaks at about 7.8, 15.7, 20.8, 23.7, 24.5, and 32.5 degrees 2Θ, further comprising peaks at about 9.9, 13.0, 14.6, 16.0, 16.9, 18.1, and 34.3 degrees 2Θ, and wherein the nanocrystals are nanoplates having the crystallographic axis normal to the surfaces that define the thickness of the nanoplates.

25. The method according to claim 21, wherein the method comprises topically applying an effective amount of the ophthalmic aqueous nanosuspension at least once a day for at least two weeks to eyelids, eyelashes or eyelid margin of a subject in need thereof.

\* \* \* \* \*